(12) United States Patent
Estes et al.

(10) Patent No.: US 8,066,710 B2
(45) Date of Patent: *Nov. 29, 2011

(54) DISTRACTOR FOR POSTERIOR INTERBODY FUSION

(75) Inventors: Bradley T. Estes, Cordova, TN (US);
Regis W. Haid, Jr., Atlanta, GA (US);
Eddie F. Ray, III, Cordova, TN (US);
Jeffrey D. Moore, Horn Lake, MS (US);
Gerald E. Rodts, Jr., Atlanta, GA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 12/798,632

(22) Filed: Apr. 8, 2010

(65) Prior Publication Data

US 2010/0198226 A1   Aug. 5, 2010

Related U.S. Application Data

(62) Division of application No. 10/268,841, filed on Oct. 10, 2002, now Pat. No. 7,722,618, which is a division of application No. 09/829,655, filed on Apr. 10, 2001, now Pat. No. 6,506,151, which is a division of application No. 09/179,799, filed on Oct. 27, 1998, now Pat. No. 6,241,729.

(60) Provisional application No. 60/081,206, filed on Apr. 9, 1998.

(51) Int. Cl.
*A61B 17/60* (2006.01)
(52) U.S. Cl. ........................................................ 606/90
(58) Field of Classification Search .................... 606/90, 606/96, 99, 102, 105
See application file for complete search history.

(56) References Cited

U.S. PATENT DOCUMENTS

| | | | |
|---|---|---|---|
| 1,708,578 A | 4/1929 | Hyde |
| 3,486,505 A | 12/1969 | Morrison |
| 4,005,527 A | 2/1977 | Wilson et al. |
| 4,350,151 A | 9/1982 | Scott |
| 4,545,374 A | 10/1985 | Jacobson |
| 4,566,466 A | 1/1986 | Ripple et al. |
| 4,921,493 A | 5/1990 | Webb, Jr. et al. |
| 4,934,352 A | 6/1990 | Sullivan, Jr. |
| 4,938,230 A | 7/1990 | Machek et al. |
| 4,985,019 A | 1/1991 | Michelson |

(Continued)

FOREIGN PATENT DOCUMENTS

EP   0796593   9/1997

(Continued)

OTHER PUBLICATIONS

"Surgical Technique Using Bone Dowel Instrumentation—For Posterior Approach", Sofamor Danek Brochure, 1996.

(Continued)

*Primary Examiner* — Eduardo C Robert
*Assistant Examiner* — Mary Hoffman

(57) ABSTRACT

A method and instrumentation for spinal interbody fusion is disclosed. The instruments and methods are particularly adapted for interbody fusion from a posterior approach to the spine. One instrument is a retractor having a lockable pivotally mounted handle. Another instrument is a template for straddling the dura. A modular distractor is also provided and preferably includes a tapered shaft with a visualization window disposed therein. Yet another instrument is a depth gauge to verify bone opening depth and dimension, preferably including a radiopaque portion. A method contemplates the use of these instruments to prepare a disc space to receive an implant.

14 Claims, 20 Drawing Sheets

U.S. PATENT DOCUMENTS

| | | |
|---|---|---|
| 5,013,318 A | 5/1991 | Spranza, III |
| 5,015,247 A | 5/1991 | Michelson |
| D318,629 S | 7/1991 | Michelson |
| 5,035,232 A | 7/1991 | Lutze et al. |
| 5,055,104 A | 10/1991 | Ray |
| D325,081 S | 3/1992 | Michelson |
| 5,180,388 A | 1/1993 | DiCarlo |
| 5,195,526 A | 3/1993 | Michelson |
| 5,267,999 A | 12/1993 | Olerud |
| 5,361,766 A | 11/1994 | Nichols et al. |
| 5,379,758 A | 1/1995 | Snyder |
| 5,431,658 A | 7/1995 | Moskovich |
| 5,443,514 A | 8/1995 | Steffee |
| 5,484,437 A | 1/1996 | Michelson |
| 5,489,307 A | 2/1996 | Kuslich et al. |
| 5,490,843 A | 2/1996 | Hildwein et al. |
| 5,558,621 A | 9/1996 | Heil |
| D374,283 S | 10/1996 | Michelson |
| D377,093 S | 12/1996 | Michelson |
| 5,593,409 A | 1/1997 | Michelson |
| 5,630,816 A | 5/1997 | Kambin |
| 5,645,549 A | 7/1997 | Boyd et al. |
| 5,697,889 A | 12/1997 | Slotman et al. |
| 5,722,977 A | 3/1998 | Wilhelmy |
| 5,741,253 A | 4/1998 | Michelson |
| 5,772,661 A | 6/1998 | Michelson |
| D397,436 S | 8/1998 | Michelson |
| 5,797,909 A | 8/1998 | Michelson |
| 5,800,438 A | 9/1998 | Tuke et al. |
| D405,176 S | 2/1999 | Michelson |
| 5,885,299 A | 3/1999 | Winslow et al. |
| 5,902,233 A | 5/1999 | Farley et al. |
| 5,964,760 A | 10/1999 | Richelsoph |
| 5,976,080 A | 11/1999 | Farascioni |
| 5,989,289 A | 11/1999 | Coates et al. |
| 6,004,326 A | 12/1999 | Castro et al. |
| 6,042,582 A | 3/2000 | Ray |
| 6,063,088 A | 5/2000 | Winslow |
| 6,083,225 A | 7/2000 | Winslow et al. |
| 6,159,214 A | 12/2000 | Michelson |
| 6,165,219 A | 12/2000 | Kohrs et al. |
| 6,206,826 B1 | 3/2001 | Mathews et al. |
| 6,358,253 B1 | 3/2002 | Torrie et al. |
| 6,511,484 B2 | 1/2003 | Torode et al. |
| 6,592,588 B1 | 7/2003 | Bobic et al. |
| 2003/0032865 A1 | 2/2003 | Estes et al. |
| 2004/0153089 A1 | 8/2004 | Zdeblick et al. |

FOREIGN PATENT DOCUMENTS

| | | |
|---|---|---|
| GB | 2306653 A | 5/1997 |
| WO | WO 92/20294 | 11/1992 |
| WO | WO 95/21590 | 8/1995 |
| WO | WO 95/26164 | 10/1995 |
| WO | WO 96/27345 | 9/1996 |
| WO | WO 98/04202 | 2/1998 |
| WO | WO 99/63891 | 12/1999 |

OTHER PUBLICATIONS

"The Dowel Intervertebral-Body Fusion as Used in Lumbar-Disc Surgery," by B.R. Wiltberger, M.D., The Journal of Bone and Joint Surgery, 1957; pp. 284-292.

"The Prefit Dowel Intervertebral Body Fusion as Used in Lumbar Disc Therapy," by B.R. Wiltberger, M.D., American Journal of Surgery, 1953; pp. 723-727.

"Posterior Lumbar Interbody Fusion with Specialized Instruments," by Gabriel W.C. Ma, M.D.; pp. 57-63, Mar. 1985.

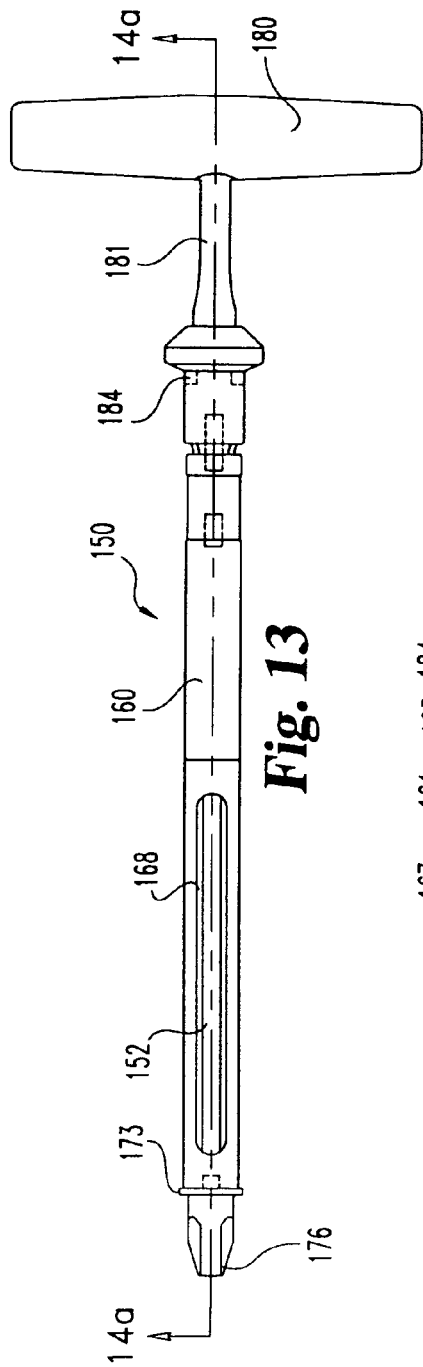
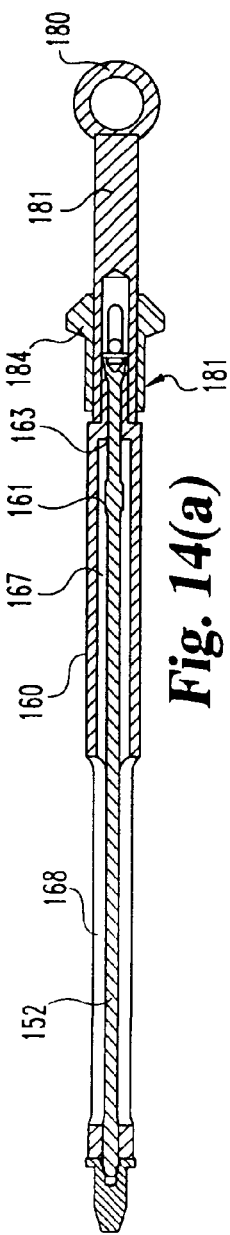
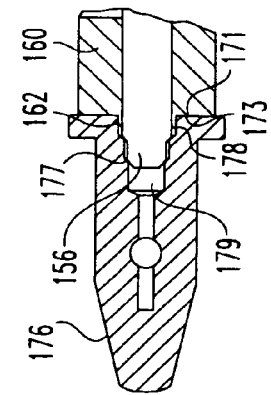
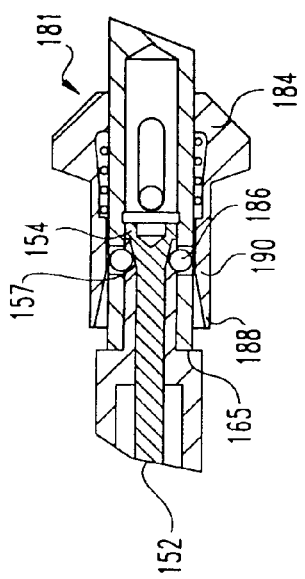
Fig. 13
Fig. 14(a)
Fig. 14(b)
Fig. 14(c)

DISTRACTOR FOR POSTERIOR INTERBODY FUSION

REFERENCE TO RELATED APPLICATIONS

This application is a divisional of U.S. patent application Ser. No. 10/268,841 filed Oct. 10, 2002 now U.S. Pat. No. 7,722,618, which is a divisional of U.S. patent application Ser. No. 09/829,655 filed Apr. 10, 2001, now U.S. Pat. No. 6,506,151, which is a divisional of U.S. patent application Ser. No. 09/179,799 filed Oct. 27, 1998, now U.S. Pat. No. 6,241,729, which in turn claims the benefit of U.S. Provisional Application No. 60/081,206 filed Apr. 9, 1998, the contents of each application hereby incorporated by reference in its entirety.

BACKGROUND OF THE INVENTION

The present invention relates generally to surgical procedures for spinal stabilization and more specifically to instrumentation and techniques for inserting a spinal implant within the intervertebral disc space between adjacent vertebra. More particularly, while aspects of the present invention may have other applications, the invention provides instruments and techniques especially suited for interbody fusion from a generally posterior approach to the spine Various surgical methods have been devised for the implantation of fusion devices into the disc space. Both anterior and posterior surgical approaches have been used for interbody fusions. In 1956, Ralph Cloward developed a method and instrumentation for anterior spinal interbody fusion of the cervical spine. Cloward surgically removed the disc material and placed a tubular drill guide with a large foot plate and prongs over an alignment rod and then embedded the prongs into adjacent vertebrae. The drill guide served to maintain the alignment of the vertebrae and facilitated the reaming out of bone material adjacent the disc space. The reaming process created a bore to accommodate a bone dowel implant. The drill guide was thereafter removed following the reaming process to allow for the passage of the bone dowel which had an outer diameter significantly larger than the reamed bore and the inner diameter of the drill guide. The removal of the drill guide left the dowel insertion phase completely unprotected. Thus, Cloward's method and instrumentation was designed for and limited to an anterior surgical approach and was inappropriate for a posterior application.

Furthermore, B. R. Wilterberger described in a paper entitled "Dowel Intervertebral Fusion as Used in Lumbar Disc Surgery" (published in *The Journal of Bone and Joint Surgery*, volume 39A, pgs. 234-92, 1957), the unprotected drilling of a hole from a posterior approach into the lumbar spine between the nerve roots and across the disc space, and then inserting a bone dowel into that disc space. While Wilterberger had taken the Cloward concept of circular drilling followed by dowel fusion and applied it to the lumbar spine from a posterior approach, he had not further improved the method, nor had he advanced the instrumentation to provide adequate protection for the sensitive vessels and neurological structures adjacent to the operating field.

U.S. Pat. No. 5,484,437 to Michelson discloses a technique and associated instrumentation for inserting a fusion device from a posterior surgical approach that provides greater protection for the surrounding tissues and neurological structures during the procedure. As described in more detail in the '437 patent, the surgical technique involves the use of a distractor having a penetrating portion that urges the vertebral bodies apart to facilitate the introduction of the necessary surgical instrumentation. The '437 patent also discloses a hollow sleeve having teeth at one end that are driven into the vertebrae adjacent the disc space created by the distractor. These teeth engage the vertebra to maintain the disc space height during subsequent steps of the procedure following removal of the distractor. In accordance with one aspect of the '437 patent, a drill is passed through the hollow sleeve to remove portions of the disc material and vertebral bone to produce a prepared bore for insertion of the fusion device. The drill is then removed from the sleeve and the fusion device is positioned within the disc space using an insertion tool.

While the more recent techniques and instrumentation represent an advance over earlier surgical procedures for the preparation of the disc space and insertion of the fusion device, the need for improvement still remains. The present invention is directed to this need and provides convenient methods and instruments to insure safe and effective preparation of a disc space in conjunction with implant placement.

SUMMARY OF THE INVENTION

One object of the present invention is to provide an improved retractor assembly permitting variable placement of the handle with respect to a retractor blade. The retractor comprises a retractor blade, a shaft having a first portion connected to the retractor blade, and an opposite second portion pivotally connected to a handle. Preferably, the assembly further includes a locking mechanism selectively locking the handle to the second portion to limit pivotal movement of the handle in relation to the shaft.

In another aspect of the present invention, a method of dura retraction is provided for posterior access to the spine. The method comprises providing a retractor having a retractor blade pivotally connected to a handle, and the handle having a locking mechanism to selectively lock the handle to the retractor. A portion of the dura is exposed and the retractor is inserted with the handle in an insertion position and the locking mechanism in a locked position. The dura is then retracted to expose underlying spinal elements. Preferably, the locking mechanism is unlocked to allow the handle to pivot in relation to the retractor blade. In this aspect, the handle is pivoted to a holding position and locked to maintain the handle in the locked position.

Yet a further aspect of the present invention is a template for straddling the dura in a spinal surgery to facilitate marking a surgical site to gain access to the disc space in preparation for implant placement. The template comprises a body having an upper surface and a lower surface facing the dura, and an opening formed between the upper surface and the lower surface. A shaft having a first end and a second end is connected to the body and extends away from the upper surface. Preferably, a working tube is connected to the body in substantial alignment with the opening and extends from the lower surface, the tube having a first diameter. A locator extension engages the body and is spaced from the tube to provide a space for passage of the dura therebetween. The locator extension extends from the lower surface and has a second diameter that is less than the tube diameter. Optionally, the body may be formed to match the maximum area of the insertion instrumentation at the engagement with the vertebral bodies, thereby allowing marking of the bone needing removal.

Still a further object of the present invention is to provide a spinal disc space distractor assembly. Preferably, the distractor includes a tapered shaft portion. Optionally, a window may be formed through the shaft for visualization. In one form of the invention, the assembly comprises a driving portion removably coupled to a distractor tip. The driving portion is coupled to transmit rotational and longitudinal forces. Preferably the assembly includes an outer shaft having a first driving shoulder for transmitting rotational force end and an opposite second driving shoulder for receiving a rotational force. An inner shaft is slidably disposed within at least a portion of the outer shaft, the inner shaft having a first connection end and an opposite second connection end. The first connection end is disposed adjacent the first driving shoulder. The assembly further includes a distraction tip, the tip having a driving surface adapted for engagement with the first driving shoulder and a connection surface adapted for engagement with the first connection end. A handle interconnects the inner and outer shafts and maintains the tip in contact with the outer shaft. In one embodiment the outer shaft is tapered to provide greater visualization. Further, the outer shaft may have a visualization window extending there through.

It is yet a further object to provide an instrument for determining the depth and size of an opening formed between two adjacent vertebral bodies. The instrument comprises an elongated shaft and preferably a radiolucent tip attached to the shaft, the tip including at least on radiopaque marker. Preferably, the instrument includes a distal tip sized to match the diameter or shape of the opening intending to be created.

The present invention also contemplates a method of preparing a disc space and inserting an implant. The method utilizes one or more of the instruments described above to prepare the disc space for receiving an implant.

Related objects and advantages of the present invention will be apparent from the following description.

BRIEF DESCRIPTION OF THE DRAWINGS

FIG. 1(*b*) is a partial cross-sectional side view of the retractor of FIG. 1.

FIG. 2(*b*) is a side view of the retractor shaft of FIG. 1.

FIG. 3(*b*) is a bottom view of the handle of FIG. 3(*a*).

FIG. 4(*b*) is a partial cross-sectional side view of the intraoperative template of FIG. 4(*a*).

FIG. 12(*b*) is a substantially assembled perspective view of the modular distractor of FIG. 12(*a*).

FIG. 13 is a plan elevation of a fully assembled distractor of FIG. 12(*b*).

FIGS. 14(*a*) through 14(*c*) are partial cross-sectional side views taken along line 14*a*-14*a* showing the modular distractor according to FIG. 13.

FIG. 19(*b*) is a side view of the depth stop of FIG. 19(*a*) rotated 90° about its longitudinal axis.

FIG. 19(*c*) is a cross-sectional view of the depth stop of FIG. 19(*b*).

DESCRIPTION OF THE PREFERRED EMBODIMENTS

Figure 1A:
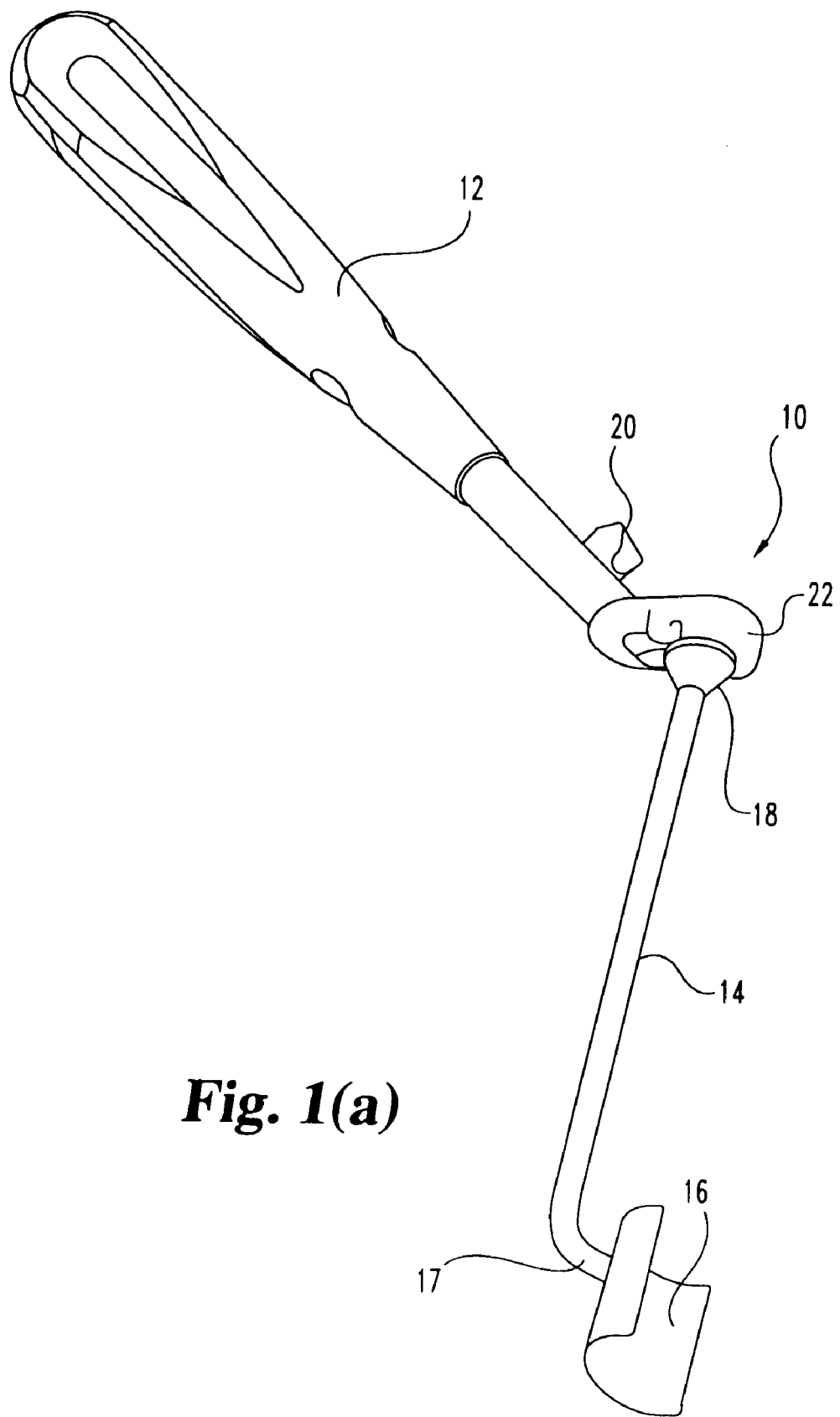
FIG. 1 (*a*) is a perspective view of a retractor according to the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention relates generally to instruments and methods for performing vertebral interbody fusion. While it should be understood that the instruments disclosed herein may have many uses, it is particularly contemplated that they may be used to perform vertebral interbody fusion from a generally posterior approach to the spine. Such procedures typically involve the placement of dowels or other implants into the intervertebral disc space to promote fusion between adjacent vertebral bodies and to stabilization of the spine. Such implants may be formed of metal, ceramics, composites, bone or other bio-compatible materials, depending on the properties desired from the implant.

Figure 2A:
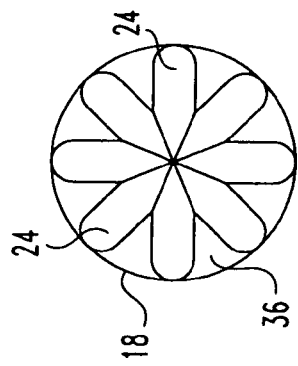
FIG. 2(*a*) is an end view of a shaft of a portion of the retractor of FIG. 1.
Figure 2B:
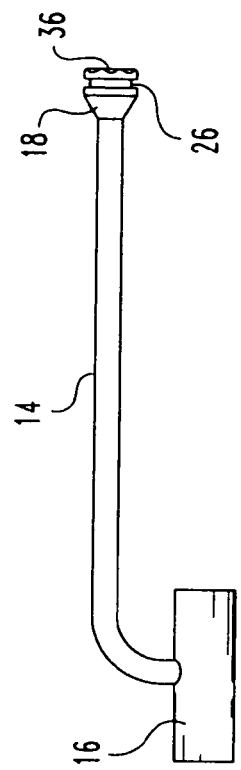
Figure 1B:
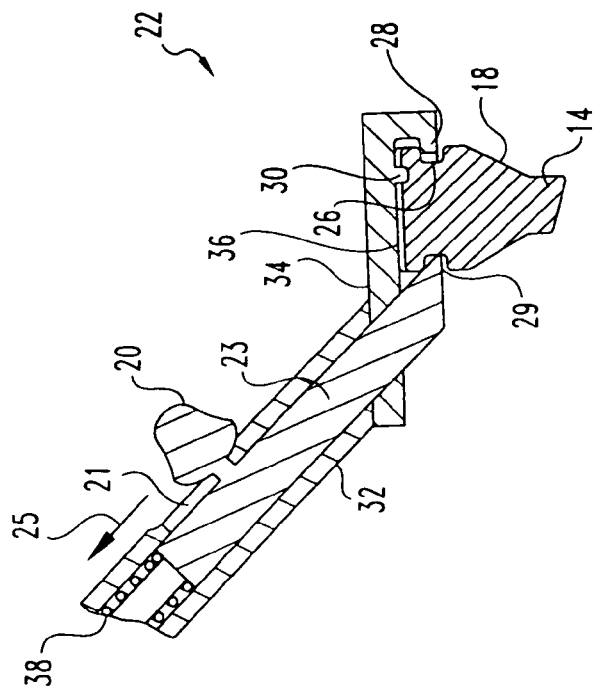

Referring now to FIG. 1(*a*), there is shown a retractor mechanism according to one aspect of the present invention. Retractor 10 includes a handle 12 pivotally connected to a shaft 14 having a distal end 17 connected to a retractor blade 16. While retractor blade 16 is shown as a semi-circular blade, it is contemplated that any of a variety of retractor blade shapes may be utilized in conjunction with handle 12 and shaft 14 of the present invention. Handle 12 is pivotable in relation to shaft 14 and may be releasably connected to shaft 14 adjacent enlarged end 18. As shown more clearly in FIG. 2, enlarged end 18 includes a series of grooves 24 on its upper surface 36. Handle 12 includes a locking mechanism 22 adapted to selectively engage annular groove 26 extending around enlarged end 18 of shaft 14, and at least one of grooves 24 disposed on the upper surface 36.

Figure 3A:
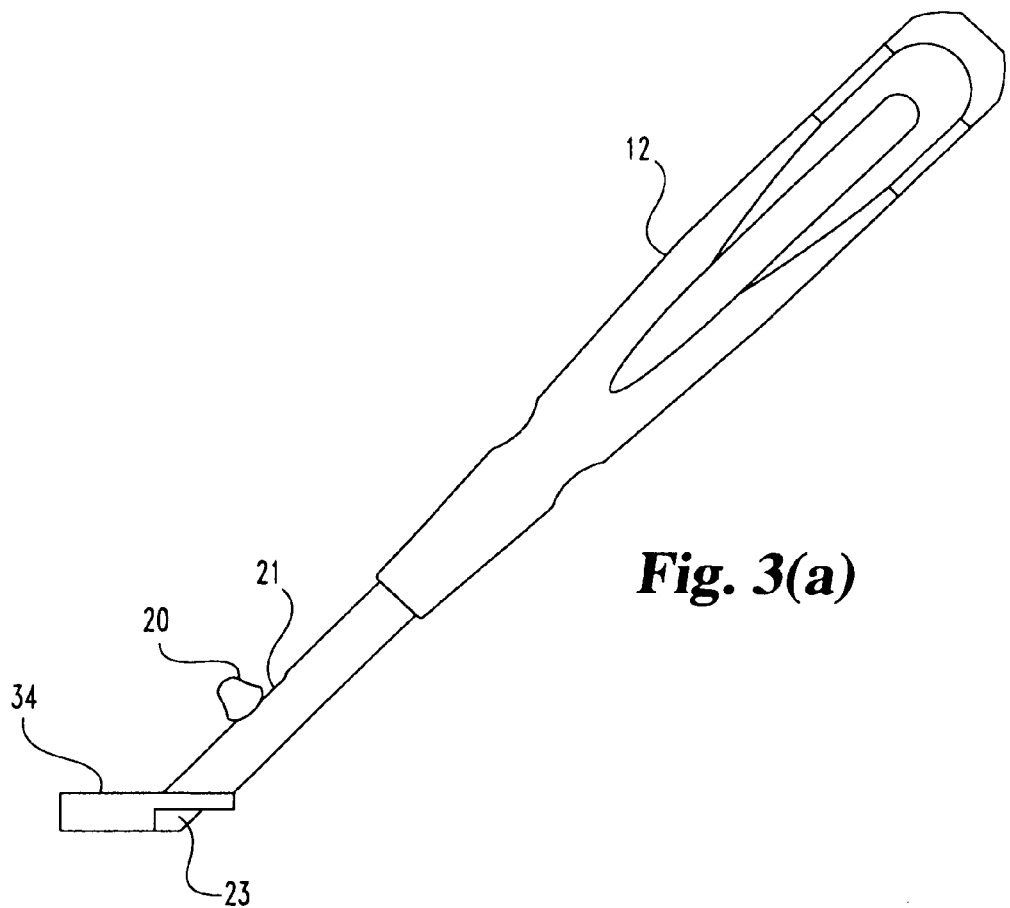
FIG. 3(*a*) is a side view of the handle of FIG. 1.
Figure 3B:
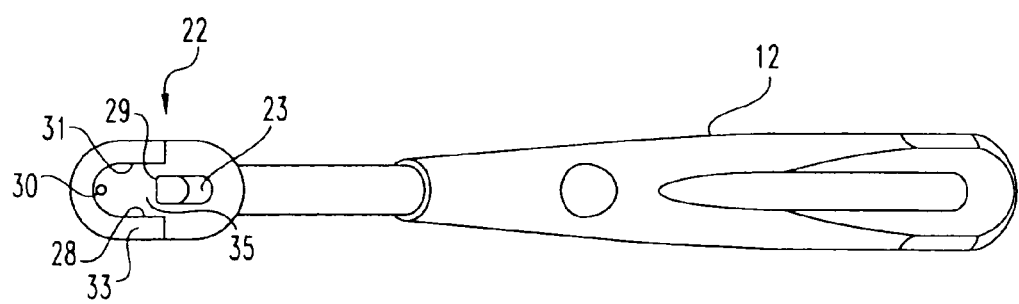

Referring specifically to FIG. 1(*b*), locking mechanism 22 includes a flange 28 adapted for engaging a portion of annular groove 26 disposed on shaft 14. As shown in FIG. 3(*b*), flange 28 extends in a semi-circular fashion and includes substantially parallel straight extensions 31 and 33 positioned adjacent opening 35. Flange 28 defines an opening 35 for receiving a portion of the enlarged head 18 of shaft 14 to hold the shaft and handle in mating engagement. Locking mechanism 22 further includes an upper plate 34 having a downwardly extending internal projection 30 adapted to engage one of grooves 24 on shaft 14. Although only a single projection 30 is shown, it will be understood that multiple projections may be provided to engage one or more grooves on shaft 14. Disposed within handle 12 is an inner shaft 23 slidable within outer shaft 32 to at least partially close opening 35 to prevent passage of enlarged end 18 from the channel formed by flange 28. The position of inner shaft 23 is controlled by movement of thumb lever 20 sliding within slot 21 formed in outer shaft 32. Inner shaft 23 includes a projection 29 adapted to engage a portion of annular groove 26. Preferably, inner shaft 23 is biased to an extended position shown in FIG. 1(*b*) by spring 38 captured within outer shaft 32. In the extended position, inner shaft 23 retains handle 12 and shaft 14 in locked engagement.

In a locked position, flange 28 of locking mechanism 22 engages a semi-circular portion of annular groove 26 and projection 29 on inner shaft 23 also engages a further portion of annular groove 26. This engagement maintains handle 12 and shaft 14 securely engaged. To inhibit pivotal movement in the locked position, grooves 24 on enlarged end 18 are urged into engagement with projection 30 of locking mechanism 22, thereby positioning the projection in one of the grooves 24 to prevent rotation of handle 12 about the longitudinal axis of shaft 14. In an adjustment position, projection 29 may be partially withdrawn from annular groove 26 by movement of thumb lever 20 in the direction of arrow 25. With projection 29 in the adjustment position, there may be sufficient transverse movement of shaft 14 within opening 35 to disengage projection 30 from grooves 24 thereby permitting pivotal movement of handle 12 in relation to shaft 14 without complete removal of the handle. In the adjustment position, inner shaft 23 prevents movement of shaft 14 entirely out of opening 35, thus maintaining the connection between handle 12 and shaft 14. With the locking mechanism in the adjustment position, the handle may be pivotally repositioned to a variety of positions. It will be understood that in a preferred embodiment, shaft 14 includes eight grooves 24, thereby permitting handle 12 to be locked in eight separate pivotal positions about shaft 14. Although eight grooves 24 are shown, it is contemplated that more or less grooves may be provided to accommodate various positions. Moreover, while grooves are shown on the top of shaft 14, it is contemplated that these may be placed around the exterior of enlarged head 18 to engage a projection correspondingly disposed in locking mechanism 22. Further, the placement of grooves and projections may be reversed such that the shaft includes one or more projections mating with grooves in the locking mechanism. Other mechanisms known to those skilled in the art for allowing selective pivotal movement between the shaft and handle are contemplated and come within the scope of the present invention.

In an unlocked position, projection 29 of inner shaft 23 is completely withdrawn from opening 35 by further movement of thumb lever 20 in the direction of arrow 25, thereby allowing enlarged end 18 to be removed from locking mechanism 22. The locking mechanism may also be placed in the unlocked position to insert a tool shaft.

Utilization of the above-described retractor device provides several advantages over retractors utilizing a fixed handle position. Specifically, in a first locked handle position, a surgeon may position the retractor device 10 to most effectively retract a desired neural structure or vessel. Once the surgeon has properly positioned the retractor adjacent the desired tissue and the tissue is retracted, handle locking mechanism 22 may be moved to the adjustment position and handle 12 pivoted about shaft 14 to a position for an assistant to maintain the tissue or vessel in the retracted position. Often, the assistant will be located on the opposite side of the patient from the surgeon and it is desirable that the handle be rotated out of the surgical field to provide the best access and visualization of the surgical site for the surgeon. Once properly positioned, the locking mechanism may be returned to the locked position to securely hold the handle and shaft in the selected arrangement. Further, handle 12 may be removed from shaft 14 and utilized with a variety of instruments, such as those disclosed further herein. Use of a removable handle having the advantages described above may limit the total number of handles required for a surgical procedure or that must be supplied with a surgical set.

Figure 4A:
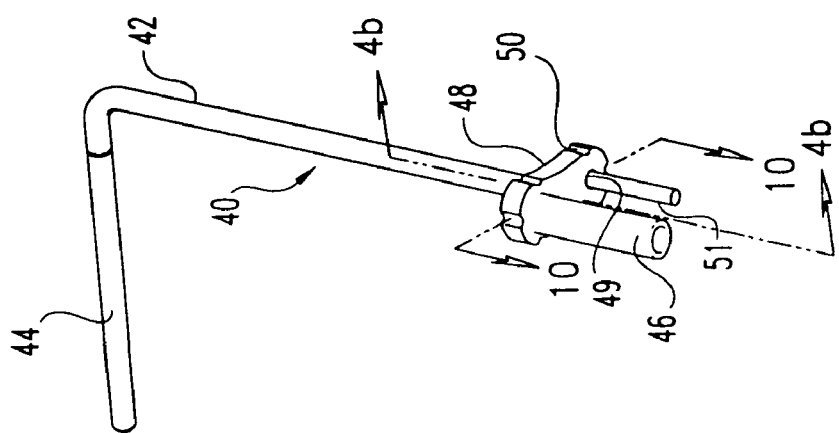
FIG. 4(*a*) is a perspective view of an intraoperative template according to another aspect of the present invention.
Figure 4B:
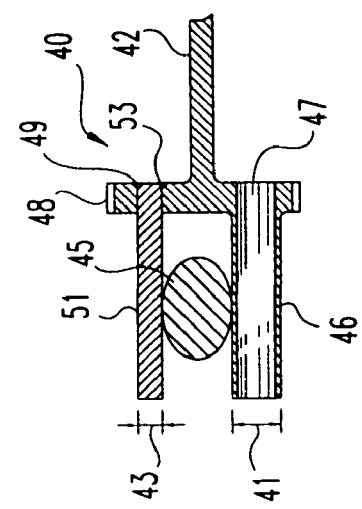

Referring now to FIGS. 4 (*a*) and (*b*), there is shown an intraoperative template 40 according to another aspect of the present invention. Template 40 includes a shaft 42 interconnected with handle 44. Shaft 42 is centrally connected to the upper side of template body 48. Template body 48 defines a number of bone marking notches 50 around its perimeter and includes an integrally formed guide tube 46 extending from its lower surface. Although an integrally formed guide tube is shown in a preferred embodiment, it will be understood that a removable guide tube may be connected adjacent an aperture in the body. Guide tube 46 defines a channel 47 to receive an instrument. Body 50 further defines an opening 49 adapted to receive a locator extension 51.

In FIG. 4(*b*) there is shown a partial cross-sectional view of the template of FIG. 4(*a*). Inserted within opening 49 is a removable locator extension 51 having a head 53. In a preferred embodiment locator extension 51 may be threadably received with opening 49 to prevent dislodgment. Diameter 41 of guide tube 46 is substantially larger than diameter 43 of locator extension 51. The additional space created by utilization of a locator extension rather than a second guide tube sized to receive a cutting instrument limits the amount of compression that the dura 45 must undergo and increases the possibility that such a template may be utilized. Preferably, guide tube 46 and locator extension 51 are in substantially parallel alignment.

Figure 5:
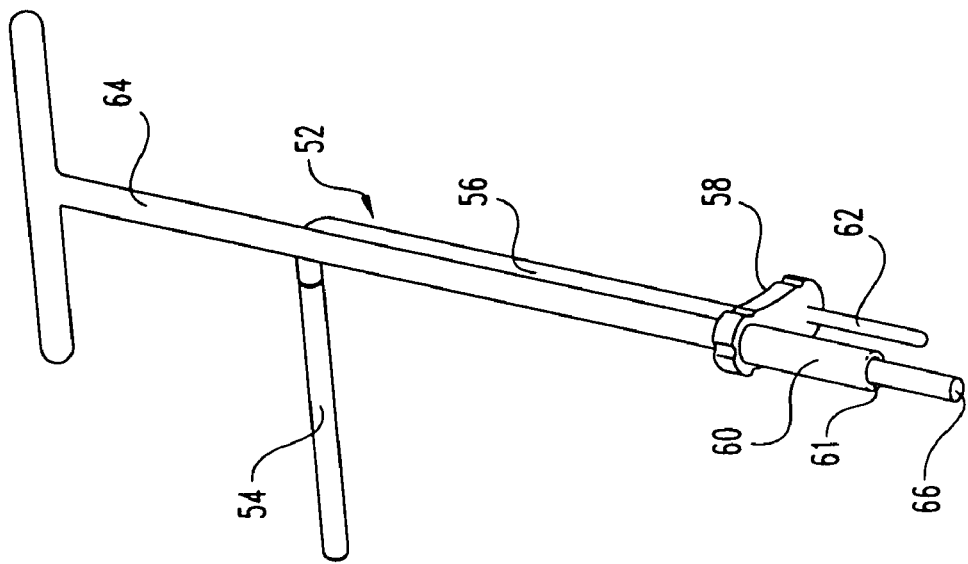
FIG. 5 is a perspective view of a further embodiment of an intraoperative template according to the present invention.

Referring now to FIG. 5, there is disclosed a second embodiment of an intraoperative template according to the present invention. A second template 52 includes a handle 54 connected to a shaft 56 which is centrally connected to template body 58. Template body 58 further includes guide tube 60 and integrally formed post 62. A trephine 64 is illustrated extending into and through guide tube 60 with trephine cutting head 66 extending beyond distal end 61 of guide tube 60. The addition of post 62 to the template permits a surgeon to straddle the dura and place post 62 to further assist in the alignment of any further trephining procedures.

Figure 10:
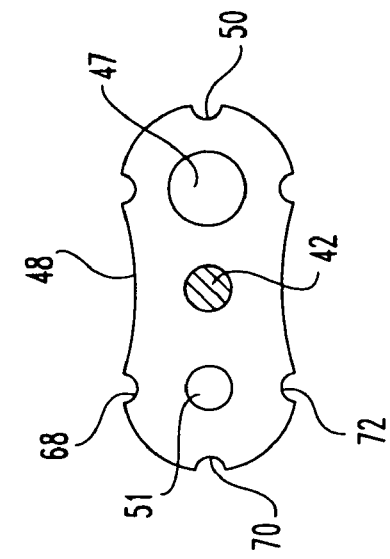
FIG. 10 is a cross-sectional view of the embodiment of FIG. 4(*a*).

Referring now to FIG. 10, template body 48 includes six indentations 50 along the perimeter of the device. The perimeter of the device matches the amount of exposure required for placement of a pair of implants. Preferably, the body is sized to match the space needed to place two cylindrical bone dowels. Therefore, if in placing template body 48, bony structures are encountered which extend into the area needed for implant placement, notches 68, 70, 72, and similar notches on the other portion of the template permit marking of the interfering structure and ultimately passage of a working channel for placement of interbody fusion devices.

Figure 6:
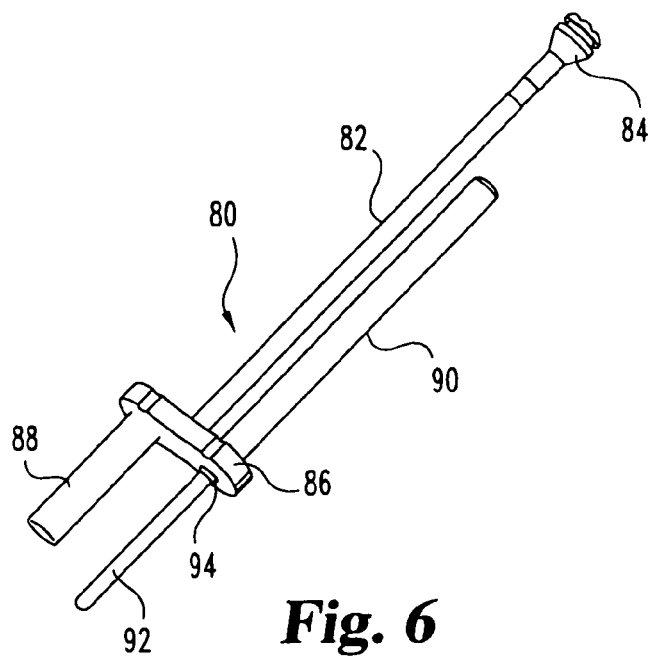
FIG. 6 is a perspective view of still a further embodiment of an intraoperative template according to the present invention.
Figure 7:
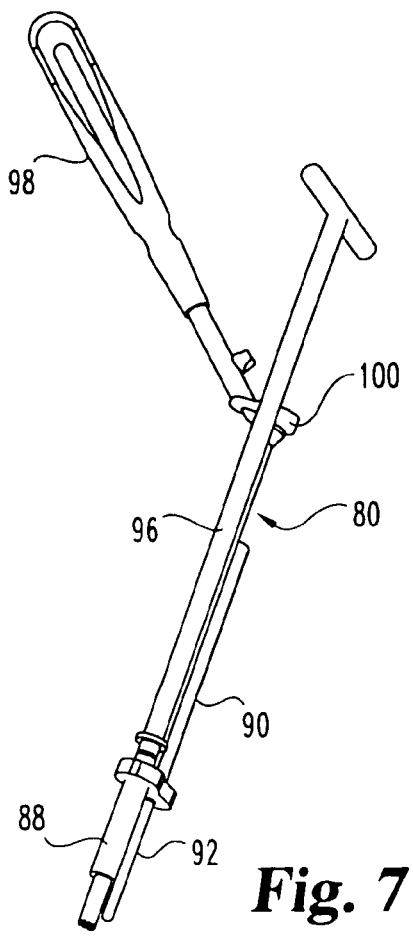
FIG. 7 is perspective view of the intraoperative template of FIG. 6 with handle and trephine.

FIGS. 6 and 7 illustrate still a further embodiment of an intraoperative template according to the present invention. Intraoperative template 80 includes a shaft 82 and an enlarged end 84 similar to the enlarged end 18 previously described on shaft 14 of the retractor mechanism disclosed in FIG. 1. As such, handle 98 is identical to handle 12 and may be pivotally positioned on shaft 82. Intraoperative template 80 includes a template body 86, a guiding tube 88, and an aperture 94 extending through template body 86. As shown in FIG. 6, a removable post 92 with attached handle 90 has been placed in opening 94 to drop into a first trephine hole or to penetrate the disc annulus to stabilize the template during trephining of a first hole through guide tube 88. It will be understood that post 92 and handle 90 may be removed for unilateral templating if desired.

Referring now to FIG. 7, there is shown the intraoperative template of FIG. 6 with interconnected handle 98 joined by connection mechanism 100 as previously described with respect to the retractor mechanism of FIG. 1. A trephine 96 is further disclosed extending through guide tube 88.

Figure 8:
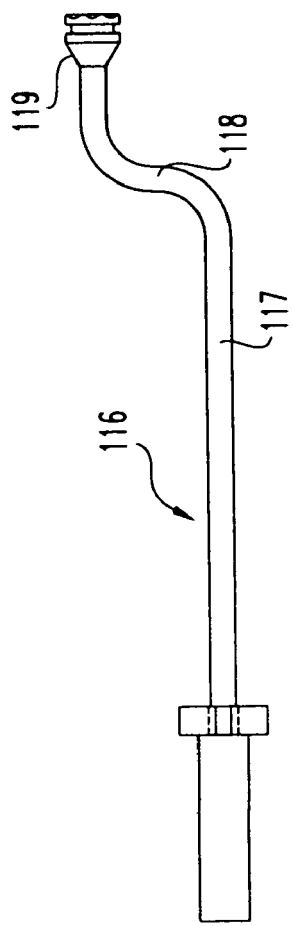
FIG. 8 is a perspective view of yet a further embodiment of an intraoperative template according to the present invention.

In FIG. 8 there is illustrated a further embodiment of a template according to the present invention. Template 116 has a template body and guide tube as previously described with respect to FIG. 6. In this embodiment, shaft 117 includes an offset portion 118 laterally offsetting enlarged head 119 from the lower portion of the shaft. It will be understood that this limits the amount of instrumentation within the surgical field and permits greater access.

Figure 9:
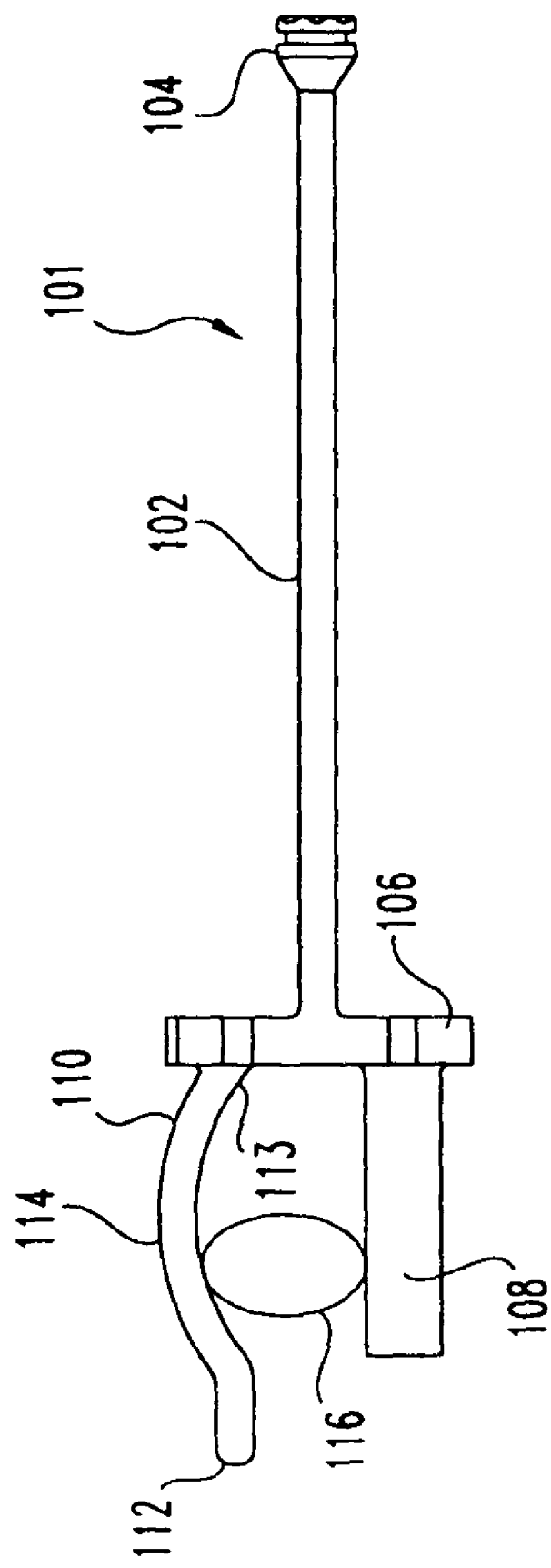
FIG. 9 is a perspective view of still a further intraoperative template.

Referring now to FIG. 9, there is shown yet a further embodiment of an intraoperative template according to another aspect of the present invention. Intraoperative template 101 includes a connection mechanism 104 on shaft 102, a template body 106, guiding tube 108, and a post 110. In contrast to the previous embodiments, post 110 includes a substantially straight portion 112 in substantial alignment with the connection 113 of post 110 to template body 106. Between straight section 112 and connection 113, is a laterally extending curved portion 114. It will be understood that the curvature of rod 112 away from tube 108 provides still further space for disposing the dura 116 between tube 108 and post 110 during the templating procedure. Post 110 may be removably secured to body 106. Moreover, post 110 is illustrated having a particular curve, it being understood that the locator extension may take an alternative configuration and remain within the scope of the present invention.

Figure 11:
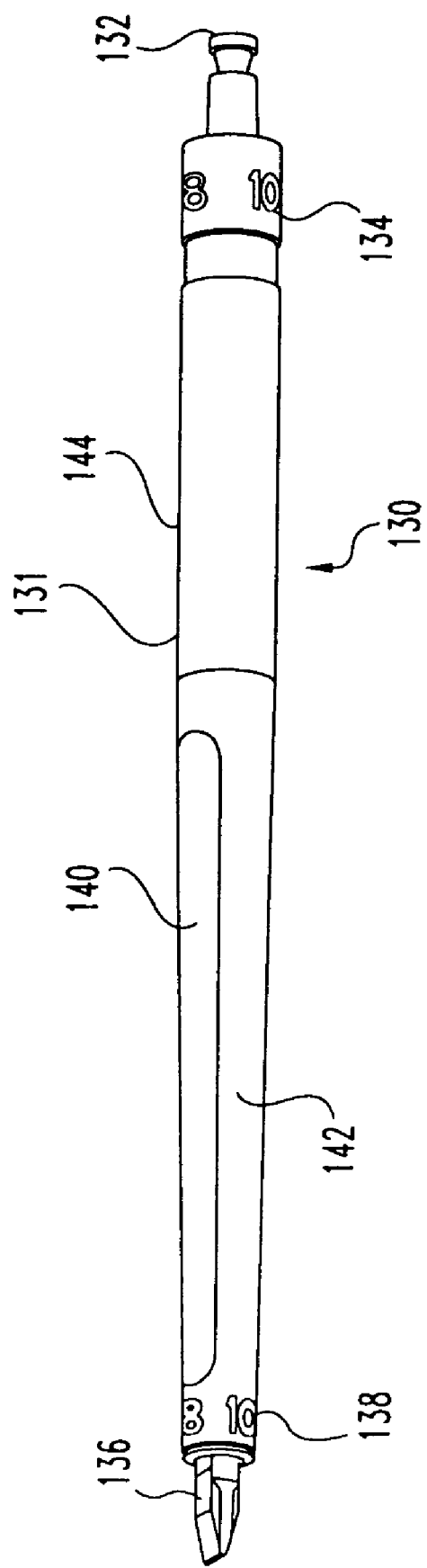
FIG. 11 is a perspective view of a distractor according to the present invention.

Referring now to FIG. 11, there is shown a distractor according to another aspect of the present invention. Distractor 130 includes a shaft 131 with a Hudson-type connection 132 and markings 134 indicating the distraction height created in the disc space by the distraction tip 136. Disposed adjacent indicators 134 is a substantially uniform diameter guiding portion 144. Extending further towards distraction tip 136 is a continuously tapering portion 142. Disposed adjacent distractor tip 136 is a further set of indicators 138, again indicating the height of distraction in the disc space created by the orientation of tip 136. Disposed within tapering section 142 is a visualization window 140 extending entirely through shaft 131 permitting visualization of structures and vessels on the opposite side of the shaft. The distractor tip of FIG. 11 is a two-position distractor having an insertion position with a first working distraction height. If the first working distrac-tion height is insufficient or a greater distraction is desired, the shaft may be rotated 90° to a second greater working distraction height.

Figure 12A:
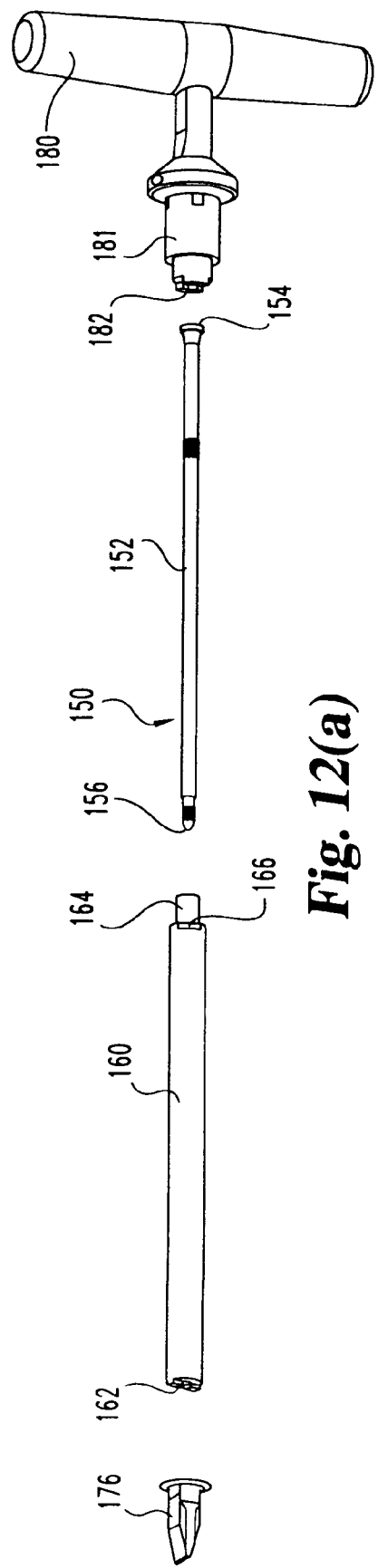
FIG. 12(*a*) is an exploded perspective view of a modular distractor according to the present invention.
Figure 12B:
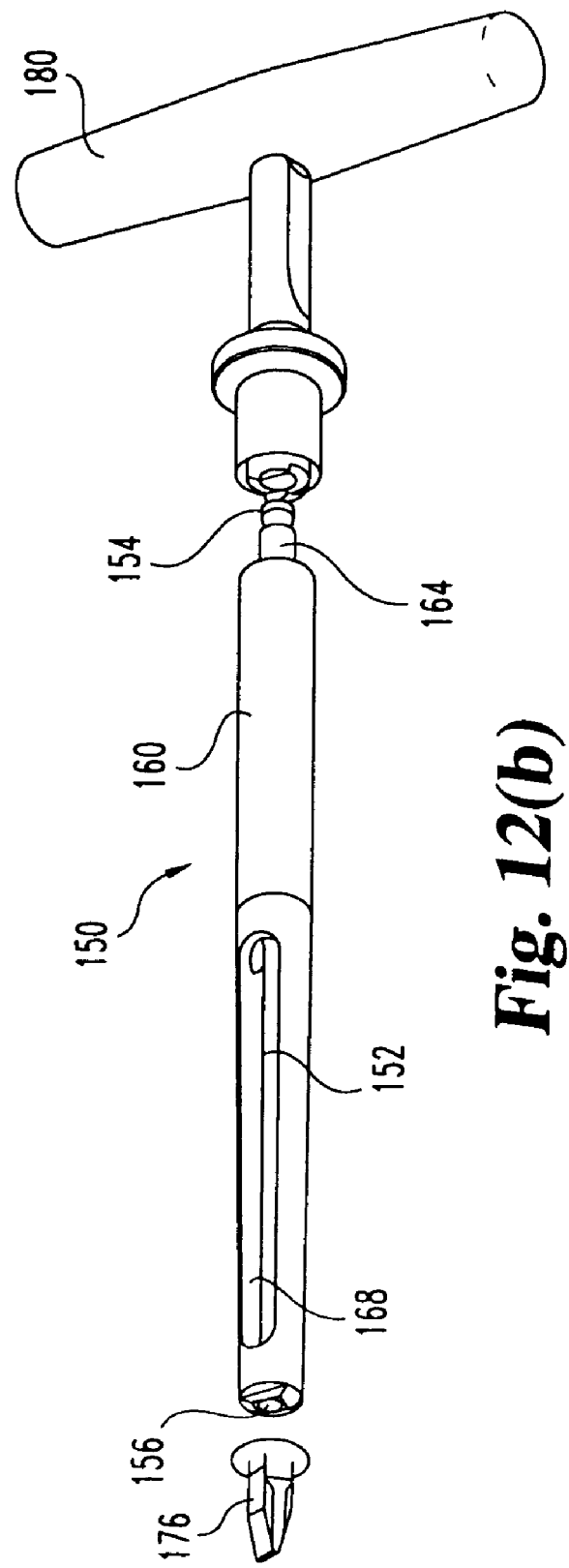

Referring to FIGS. 12 through 14, there is disclosed a modular distraction assembly 150 permitting interchangeability of distraction tips, as well as the ability to leave the distraction tip disposed within the disc space while removing the insertion tool. Referring more specifically to FIG. 12(*a*), the modular distraction assembly 150 includes a T-handle 180 with a conventional Hudson-type connection mechanism 181 disposed therein. The assembly further includes an inner shaft 152 having an enlarged end 154 adapted for engagement with Hudson mechanism 181 and an opposite threaded end 156. Inner shaft 152 may be disposed within outer tube 160. Outer tube 160 includes a slot driver 162 and an opposite end driving extension 164 having flats 166 for engagement with the T-handle 180 to transmit rotational force to outer tube 160. Preferably, outer tube includes a visualization window 168 extending therethrough. Distractor tip 176 has an internal channel 179 defining internal threads 177 for engagement with threaded end 156 of inner shaft 152 and a slot 178 for engagement with the slot driver of outer tube 160 (see FIG. 14(*c*)).

Referring now to FIGS. 14(*a*) through (*c*), there is shown a cross-section of the assembled modular distraction assembly 150. As shown in FIG. 14(*b*), enlarged end 155 of inner shaft 152 is advanced past balls 186 such that the balls are adjacent a smaller outer diameter 157 of the inner shaft 152. Collar 184 is then advanced towards outer tube 160 such that inclined surfaces 188 extend below balls 186 and reduced internal diameter portion 190 is disposed adjacent balls 186 to forcibly urge balls 186 against reduced outer diameter 157 of shaft 152. It will be understood that the engagement of balls with inner shaft 152 securely holds the inner shaft in position. Handle 180 includes a shaft portion 181 having a configuration adapted to engage the driving flats of extension 164. It will be understood that with collar 184 substantially advanced towards shoulder 165, the inner shaft and outer tube are substantially engaged with handle 180. To complete the engagement in a preferred embodiment, inner shaft 152 must be threadedly engaged with distraction tip 176 prior to attachment of T-handle such that the distal end 171 of outer tube 160 engages the enlarged head 173 of distraction tip 176 to secure the outer tube 160 in engagement with handle 180. It will be understood that to disengage the assembly, collar 184 must be pulled toward handle 180 until balls 186 are adjacent inclined surfaces 188 and allowed to move away from inner shaft 152. In this position, handle 180 may be displaced longitudinally away from outer tube 160 and removed. Once handle 180 has been removed, inner shaft 152 may be rotated to threadedly disengage from distractor tip 176, thereby allowing the inner shaft and outer tube 160 to be disengaged from distractor tip 176. Inner shaft 152 is preferably retained within outer tube 160 by threads 161. Threads 161 are larger than the internal diameter of threaded opening 163. For complete removal, threads 161 may be threadedly passed through threaded opening 163.

Figure 15:
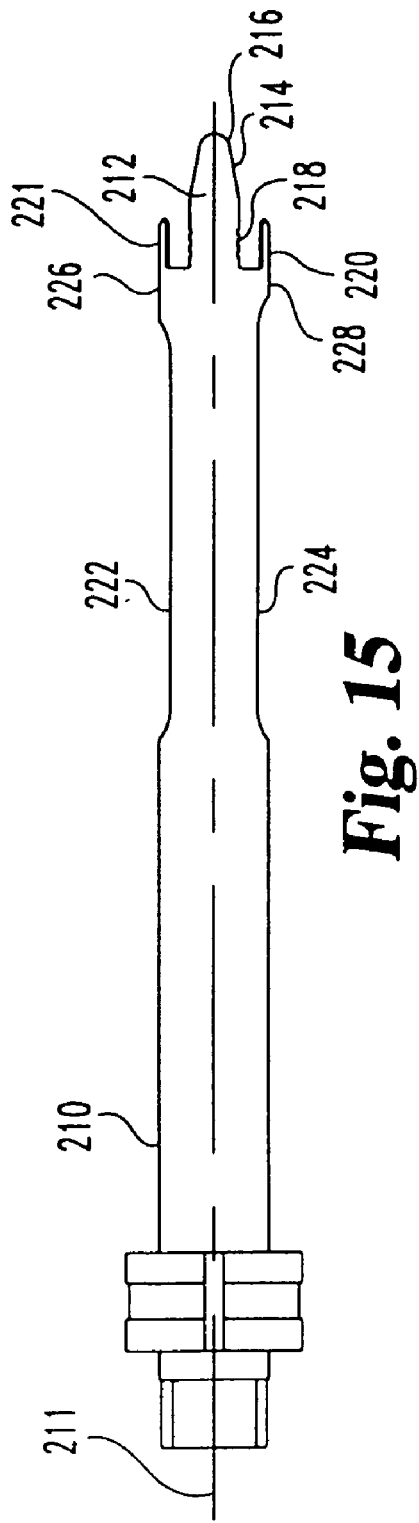
FIG. 15 is a side elevational view of an outer sleeve according to the present invention.
Figure 16:
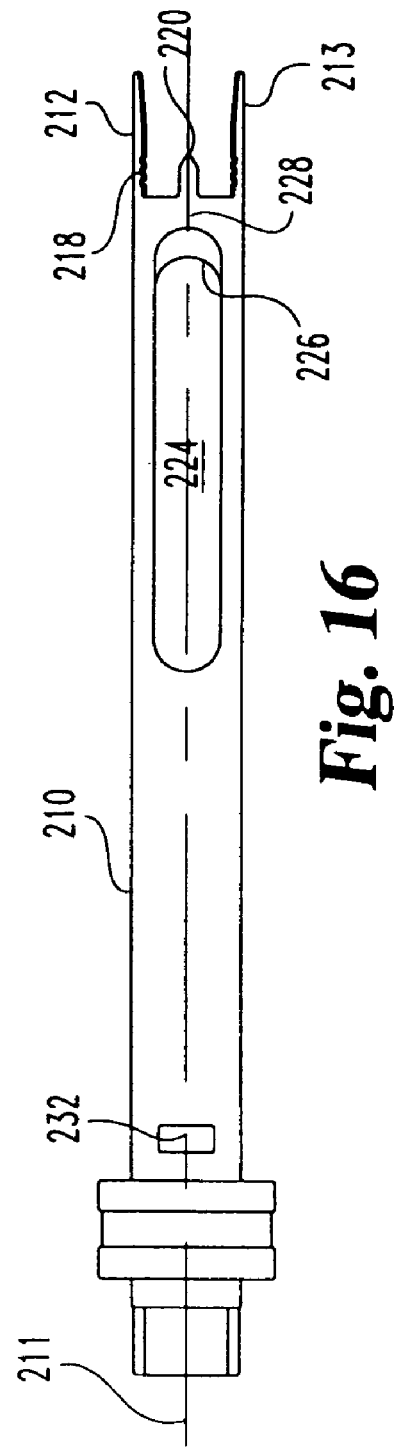
FIG. 16 is a side view of the outer sleeve of FIG. 15 rotated 90° about the longitudinal axis.

Referring now to FIGS. 15 and 16, there is shown an outer sleeve in accordance with another aspect of the present invention. Outer sleeve 210 includes a distractor portion 212 having a tip 216 and tapering portion 214 extending back to an area of grooves 218 adapted to engage adjacent bony structures. An opposing distractor portion 213 is similarly formed. The bone engaging portion further includes spikes 220 and 221 adapted to be driven into bony structures adjacent the disc space. Outer sleeve 210 further includes visualization windows 222 and 224. Window 222 extends to extended side wall 226. In contrast, window 224 extends closer to the engagement end and terminates adjacent side wall 228. It can be seen that side wall 226 is substantially longer than side wall 228 along longitudinal axis 211. As shown in FIG. 15, the longer portion of side wall 226 is provided to engage and protect nerve roots exiting the spinal cord adjacent the surgical site. In contrast, shortened wall 28 provides greater visualization through window 224. Additionally, outer tube 210 includes a markings visualization window 232 for visualizing markings on instruments in the tube indicating the depth of instrument penetration into the disc space.

Figure 17:
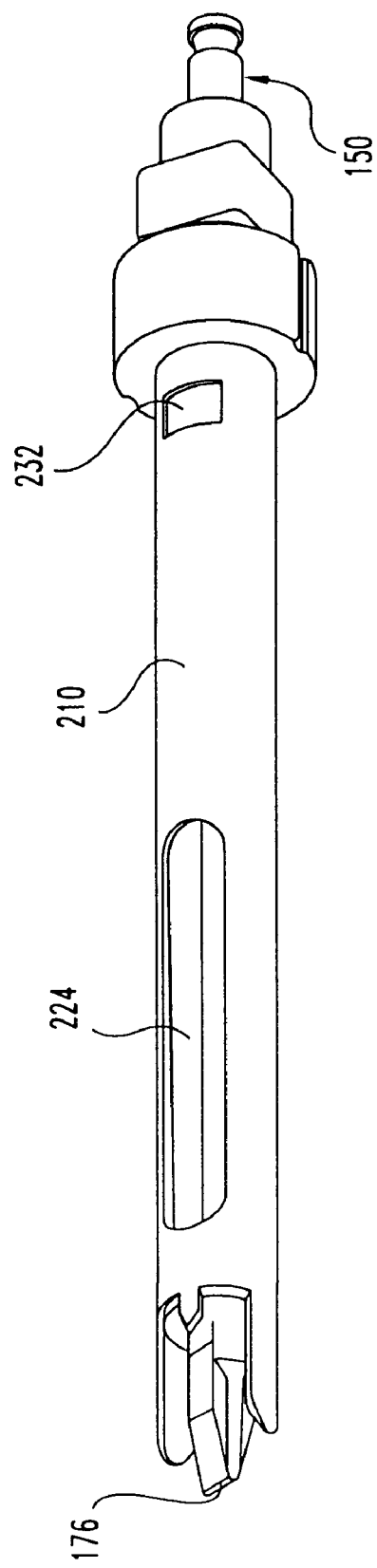
FIG. 17 is a perspective view of the outer sleeve of FIG. 15 in combination with the distractor of FIG. 13.

Referring now to FIG. 17, there is shown a combination of the distractor assembly 150 having a distractor tip 176 in combination with outer sleeve 210. Window 224 permits visualization of the distractor assembly while window 232 permits visualization of markings along the distractor assembly shaft indicating the depth of penetration of the distractor and/or outer sleeve. It will be understood that in a typical procedure, distraction assembly 150 is placed prior to the insertion and placement of outer sleeve 210.

Figure 18:
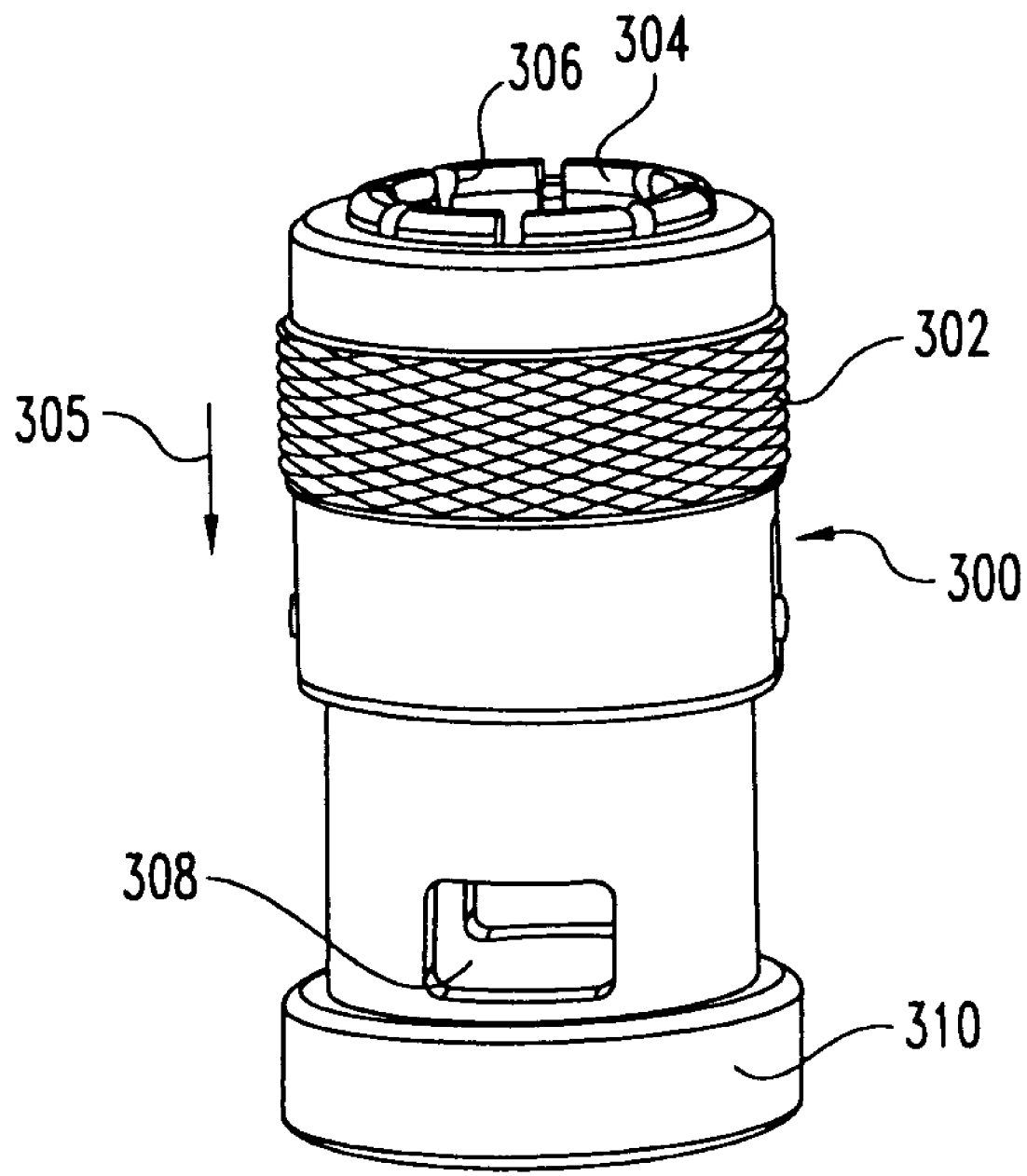
FIG. 18 is a perspective view of a depth stop according to one aspect of the present invention.
Figure 20:
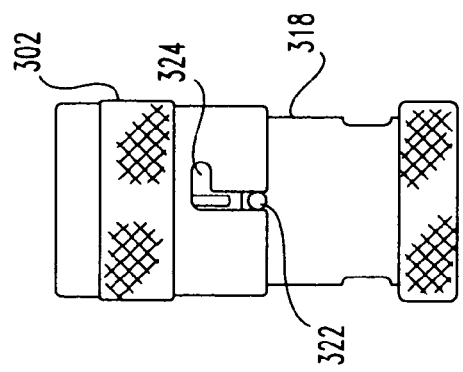
FIG. 20 is a side-elevational view of an alternative embodiment of a depth stop according to the present invention.
Figure 19C:
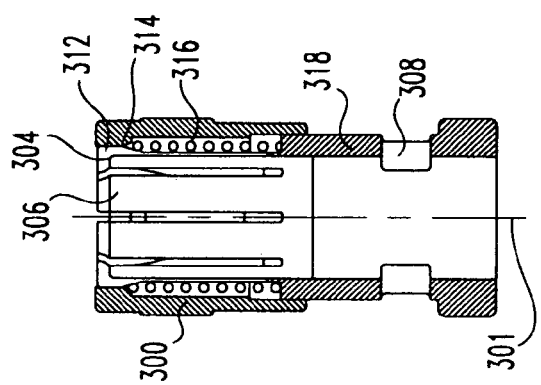
FIG. 19(*a*) is a side-elevational view of the depth stop of FIG. 22.
Figure 19B:
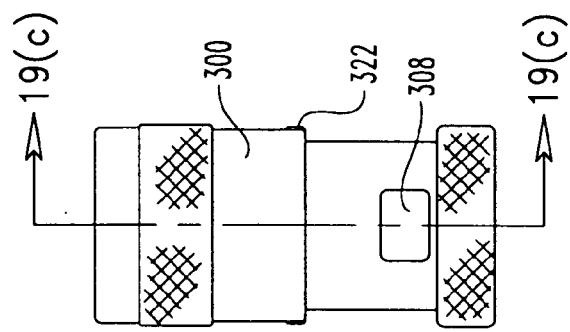

Referring now to FIGS. 18 through 20, there is disclosed a depth stop mechanism preferably cooperable with the shaft of a tool and an outer sleeve as disclosed herein. Such tools can include, without limitation, the reamer and the tap. Depth stop 300 includes an enlarged circumferential abutment shoulder 310 adapted to engage the proximal end of an outer working sleeve to prevent further advancement of the stop and any interconnected shaft. Stop 300 further includes viewing windows 308 to permit visualization of depth markings on a shaft extending within the stop. Stop 300 includes a manually operated collar 302 which may be axially displaced along axis 301 in the direction of arrow 305 to allow flexing of fingers 306. Collar 302 is normally urged into an extended position by spring 316. Referring specifically to FIG. 19(c), fingers 306 include projections 304 extending internally. The internal projections 304 are configured for engagement within grooves defined along a tool shaft of a working tool. Additionally, each finger includes an external taper portion 312 adapted for engagement with bearing surface 314 of collar 302. It will be understood that with collar 302 in a retracted position, bearing surface 314 of collar 302 will be substantially disengaged from taper 312 and thereby permits fingers 306 to disengage from the groove of a tool shaft. With collar 302 in the extended position shown in FIG. 19(c), bearing surfaces 314 bear against the tapered surface 312 of each finger to urge projections 304 into a groove of a tool shaft. In this manner, a user may quickly and easily disengage the locking mechanism of the stop to advance or retract a tool shaft and then re-engage the stop at the desired position. However, engagement with the tool shaft is indexed by the spacing of grooves on the shaft so the exact location of the stop may be easily known. The tool shaft may be rotated with respect to the stop mechanism to display the appropriate depth numeral indicated on the shaft in window 308. Preferably, collar 302 will extend at least partially beyond fingers 306 to limit the possibility that surgical staff may snag protective apparel on exposed fingers 306.

Figure 19A:
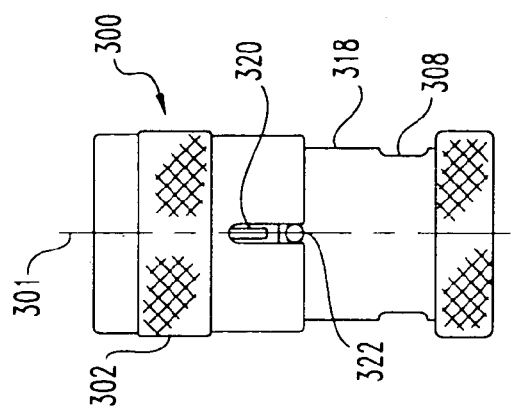

In a first embodiment shown in FIG. 19(a), collar 302 is retained on housing 306 by retaining pin 322 extending into the housing and through a slot 320. Retaining pin 322 prevents rotation of collar 232 with respect to housing 318. In an alternate embodiment shown in FIG. 24, collar 302 defines an L-shaped slot 324 which permits axial displacement of collar 302 with respect to body 318, as well as a slight amount of rotation within the slot. It will be understood that the L-shaped slot 324 permits the depth stop mechanism to be locked in a disengaged position which permits free movement of a tool shaft through the depth stop. This is a desirable construction in some instances for easy removal of the depth stop from the tool shaft, as well as for utilization of the tool without the constraints of a depth stop mechanism.

Figure 21:
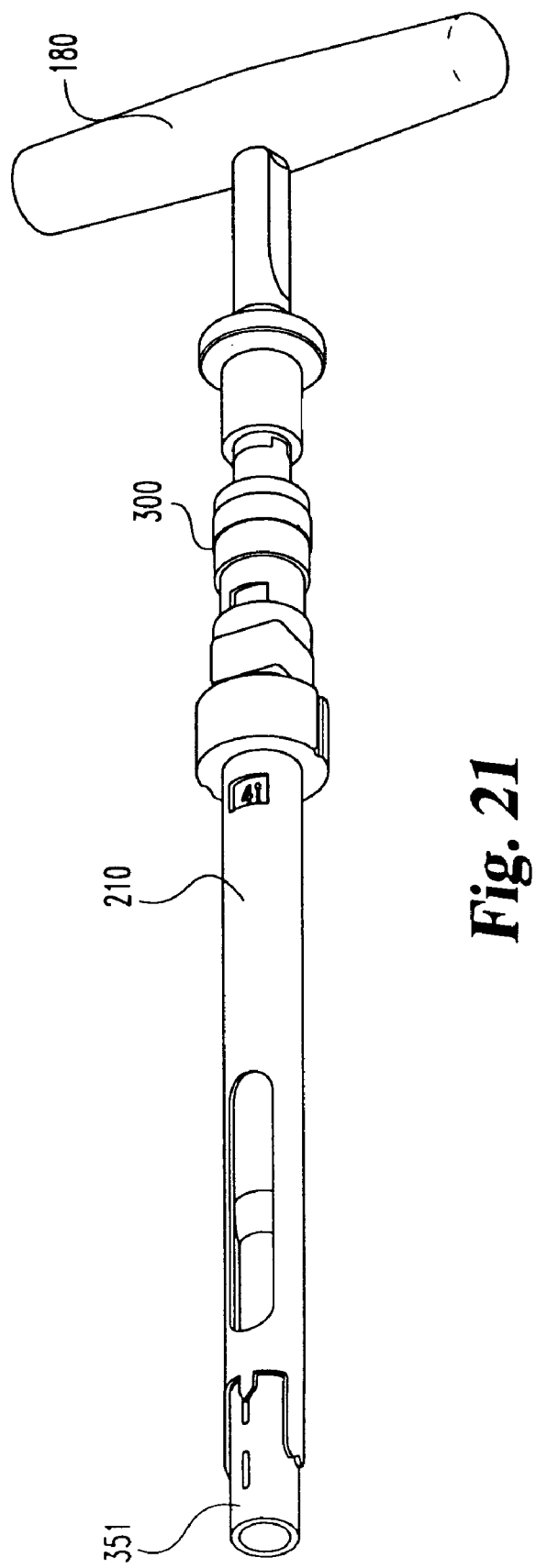
FIG. 21 is a perspective view of an outer sleeve in combination with a depth stop and reamer.

Referring now to FIG. 21, there is shown an outer sleeve 210 in combination with a depth stop 300 and reamer 351. The reamer 351 is interconnected with a T-handle 180 having Hudson connection engaged with the reamer shaft. It will be understood that depth stop 300 has been positioned to engage the upper portion of outer sleeve 210 to prevent further advancement of the reamer beyond the set depth.

Figure 22:
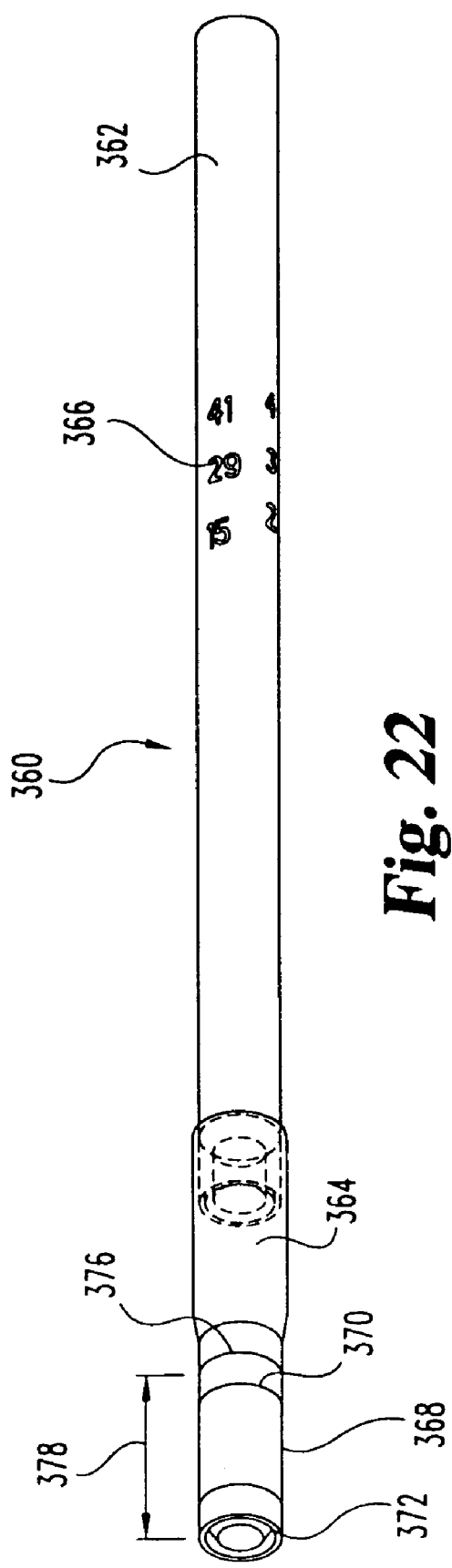
FIG. 22 is a perspective view of a depth gauge according to one aspect of the present invention.

Referring now to FIG. 22, there is shown a depth gauge according to a further aspect of the present invention. Depth gauge 360 includes an upper portion 362 having a plurality of markings 366 indicating the depth of the distal portion of the gauge into the vertebral bodies. Lower portion 364 is sized to substantially match the outer diameter of a cylindrical dowel to be inserted into an opening formed between adjacent vertebra. It will be understood that close matching of the outer diameter of depth gauge 360 with the desired diameter of the dowel to be placed, will insure that the opening formed between the vertebral bodies in the disc space is substantially clear of debris and closely matches the outer diameter of the dowel to be placed. Previously, there has been a possibility that debris could block a portion of the opening despite the fact that a depth gauge of a smaller diameter may reach the farthest reaches of the opening. In such a situation, advancement of a dowel, particularly in the case of a more brittle bone dowel, may be impeded by the debris left in the opening, resulting in the possibility of damage to the dowel and/or the opening when excessive force is applied to advance the dowel. In a further aspect of the present invention, portion 364 is radiolucent and includes a number of markers to identify the location of the depth gauge by radiographic means. Radiomarker 372 indicates the most distal position of the depth gauge and subsequent position of the implant. Radiographic markings 370 and 376 indicate the proximal ends of various sizes of implants. The distance 378 between 372 and 370 is approximately 20 mm, a conventional implant size, while the distance between 372 and line 376 is approximately 26 mm, a further conventional implant length.

Figure 23:
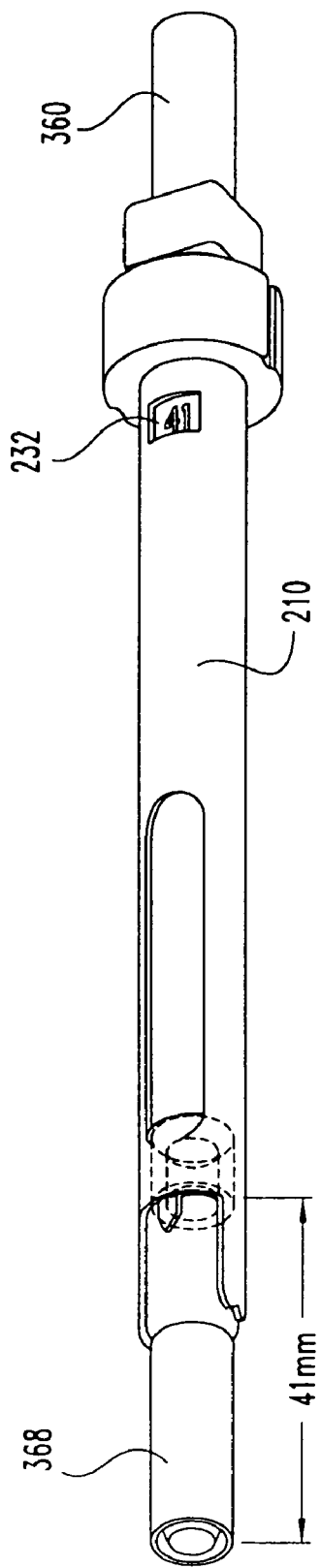
FIG. 23 is a perspective view of the depth gauge of FIG. 22 in combination with an outer sleeve.

Referring now to FIG. 23, there is shown the depth gauge of FIG. 22 inserted into and extending beyond outer sleeve 210. The depth of extension beyond outer sleeve 210 of depth gauge 360 is shown by the numeral in window 232 in the outer sleeve.

Figure 24:
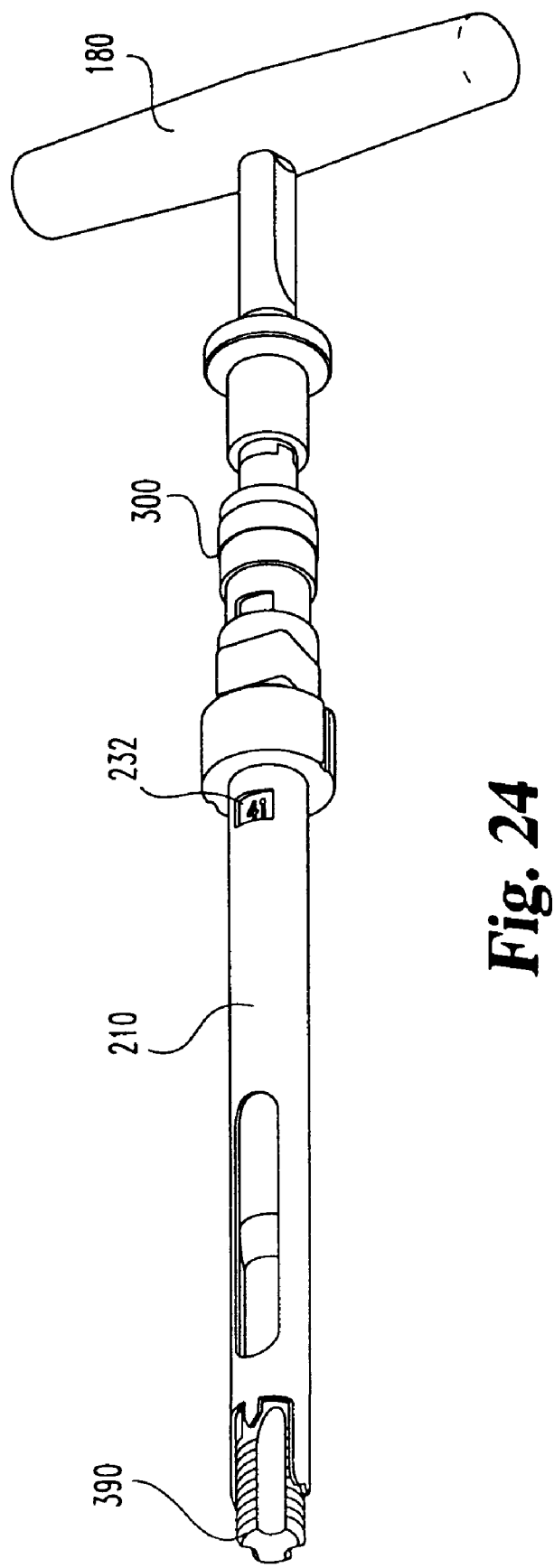
FIG. 24 is a perspective view of a tap in combination with an outer sleeve.

FIG. 24 illustrates a tap 390 interconnected with the shaft and handle 180 extending through outer sleeve 210. It will be understood that markings on the shaft of the tap may be displayed in window 232 to indicate the length of extension beyond the outer tube. Additionally, the assembly includes an adjustable depth stop 300 which engages the proximal portion of outer sleeve 210 to prevent over-advancement of tap head 390 into the disc space.

Figure 25:
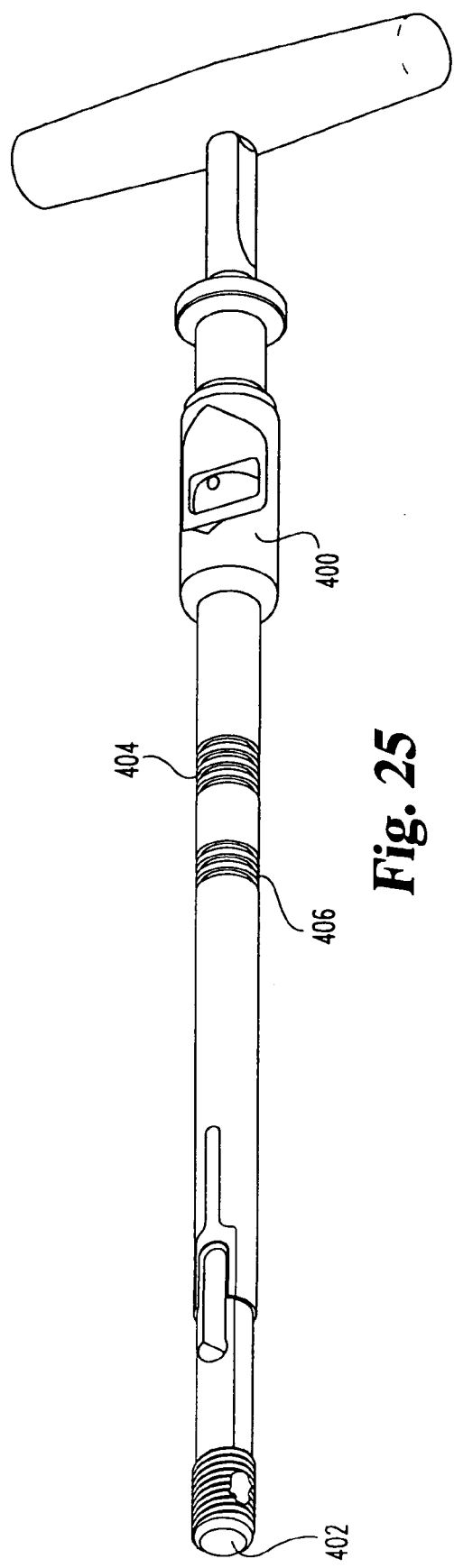
FIG. 25 is a perspective view of an implant inserter in accordance with another aspect of the present invention.

Referring now to FIG. 25, there is shown an implant insertion device 400 according to the present invention. The implant insertion device includes depth markings along the shaft of the device. Depth markings 406 indicate when the dowel is first engaged in the disc space. In the past, it was possible that when one relied only upon feel, the dowel could engage obstructions within the working channel of the outer sleeve or other type of inserting device, giving the false impression that the implant 402 was engaging the disc space and potentially leading to damage to the implant as it was forced against the obstruction. With the markings 406, multiple markings for different implant lengths, the user can visually verify whether the implant has engaged the disc space. Markings 404 are provided to indicate the depth the implant has been inserted into the disc space.

In use, an initial incision provides the approach and exposure of the posterior spinal surgical site. Exposure of the dura is accomplished in a customary fashion. In one aspect of the method according to the present invention, a retractor according to the present invention is used to retract the dura. Once retracted, the pivotal handle of the retractor is pivoted out of the way to permit an assistant to hold the retractor without interfering in the operating field.

A template in accordance with the present invention may then be placed to extend on both sides of the dura simultaneously with a guide tube positioned on one side and a locator extension positioned on the opposite side. A trephine is then passed through the guide tube and into the disc space to remove a portion of the disc and adjacent tissue. The template may be removed and repositioned to again straddle the dura with the locator extension in the previously trephined hole and the guide positioned on the opposite side of the dura. Again, the trephine is passed through the guide tube and into the disc space to form an opening therein. With the template remaining in position across the dura, the surrounding bone structures are evaluated for removal to permit placement of a guide sleeve. If bone elements, facet or lamina, are positioned beneath the template body, a marking device such as a cautherizer is used to mark the offending structure in one of the notches provided. After the bone structures have been marked, the template is removed and the bone removed in a conventional manner. Preferably, the template is repositioned to straddle the dura and the field is again checked to verify that a guide tube may be placed without obstruction. If not, further bone marking and removal is conducted. Once the space is prepared for guide tube placement, the template is removed.

In accordance with another aspect of the invention, a distractor is inserted into the disc space in one of the previously trephine openings. In a similar manner, a second distractor is inserted into the second trephined opening. If necessary, a distractor having two working heights is inserted in a first smaller height and rotated 90 degrees after insertion to a second larger height. Moreover, a tip having the desired configuration may be selected and mounted on the modular distraction assembly 150 prior to insertion. In some instances, the tip may be disconnected from the distractor assembly and temporarily left in the disc space.

The further description of the method will be described with respect to placement of single dowel, it being understood that the steps may be repeated on the opposite side to implant a second implant. A guide tube is positioned over the distractor and advanced until the distracting flanges are positioned in the disc space. It will be understood that the enlarged portion on the distractor shaft guides the guide tube into a concentric position about the distractor. Once the guide tube is securely seated, the distractor may be withdrawn. The disc space will then be prepared to receive an implant having a preselected length and diameter. A reamer of the appropriate diameter is selected and a depth stop according to the present invention is positioned on the shaft at the preselected depth markings. The reamer is rotatably advanced into the disc space until the depth stop engages the guide tube to limit further advancement. Preferably, a depth gauge according to the present invention is inserted to verify complete reaming to the preselected depth and removal of debris. If a threaded implant will be used. a depth stop will be positioned on a tap shaft at the preselected depth. The tap is rotatably inserted into the disc space until the depth stop engages the guide tube. The tap is removed and the depth gauge may be reinserted to verify that the proper sized opening has been formed and is substantially unobstructed. At this point an implant is inserted using the implant inserter. Once the implant is inserted, the guide tube may be withdrawn and the procedure repeated on the opposite side.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal disc space distractor assembly, the assembly comprising:
   an outer shaft having a first end and an opposite second end, said outer shaft including a first driving shoulder adjacent said first end for transmitting rotational force and an opposite second driving shoulder adjacent said second end for receiving a rotational force;
   an inner shaft slidably disposed within at least a portion of said outer shaft, said inner shaft having a first connection end and an opposite second connection end, said first connection end disposed adjacent said first end of said outer shaft;
   a distractor tip, said distractor tip having a driving surface adapted for engagement with said first driving shoulder and a connection surface adapted for engagement with said first connection end; and
   a handle having a connection mechanism removably and selectively engaged with said second connection end and a handle driving surface engaged with said second driving shoulder to transmit rotational force;
   wherein with said inner shaft connected to said distractor tip, connection of said connection mechanism with said inner shaft second connection end maintains said first driving shoulder in engagement with said driving surface and said second driving shoulder in engagement with said handle driving surface; and
   wherein said outer shaft includes a tapered portion extending from said first end and toward said second end.

2. The distractor assembly of claim 1, wherein said first end has a smaller diameter than said second end.

3. The distractor assembly of claim 1, wherein said outer shaft includes a longitudinal axis and defines a window extending through said tapered portion of said outer shaft transverse to said longitudinal axis and into communication with an axial passage extending through said outer shaft.

4. The distractor assembly of claim 1, wherein said inner shaft is captured within said outer shaft to limit movement between said outer shaft and said inner shaft.

5. The distractor assembly of claim 1, wherein said first driving shoulder of said outer shaft is defined by a projection extending axially from said first end of said outer shaft, said projection positioned within a drive slot defined by a proximal end portion of said distractor tip to rotationally engage said outer shaft with said distractor tip.

6. The distractor assembly of claim 1, wherein said first connection end of said inner shaft comprises a threaded end portion, and wherein said connection surface of said distractor tip comprises a threaded inner surface defined by an axial channel, wherein said threaded end portion of said inner shaft is threadedly engaged with said threaded inner surface of said axial channel to removably and selectively connect said distractor tip with said inner shaft.

7. A spinal disc space distractor, comprising:

a distractor tip; and a shaft assembly extending generally along a longitudinal axis and having a first end connected to said distractor tip, an opposite second end and a tapering portion disposed between said first end and said second end, said tapering portion tapering from a larger configuration to a smaller configuration proximal said first end; and wherein said shaft assembly comprises an inner shaft disposed within an axial passage extending through an outer shaft, said inner shaft and said outer shaft each engaged with said distractor tip; and wherein said outer shaft includes a distal driving end portion removably and selectively connected to said distractor tip; and wherein said inner shaft includes a distal connection end portion removably and selectively connected to said distractor tip; and wherein said distal driving end portion of said outer shaft is defined by an axial projection, said axial projection positioned within a drive slot defined by a proximal end portion of said distractor tip to rotationally engage said outer shaft with said distractor tip.

8. A spinal disc space distractor, comprising:

a distractor tip; and a shaft assembly extending generally along a longitudinal axis and having a first end connected to said distractor tip, an opposite second end and a tapering portion disposed between said first end and said second end, said tapering portion tapering from a larger configuration to a smaller configuration proximal said first end; and wherein said shaft assembly comprises an inner shaft disposed within an axial passage extending through an outer shaft, said inner shaft and said outer shaft each engaged with said distractor tip; and wherein said outer shaft comprises a cylindrical tube, and wherein said tapering portion tapers outwardly from a smaller diameter adjacent said first end to a larger diameter toward said second end, and wherein said tapering portion defines a window extending therethrough in a direction transverse to said longitudinal axis and into communication with said axial passage.

9. A spinal disc space distractor, comprising:

a distractor tip; and a shaft assembly extending generally along a longitudinal axis and comprising a handle, an outer tube defining an axial passage and an inner shaft at least partially disposed within said axial passage, said outer tube including a proximal driving end portion non-rotationally connected to said handle and a distal driving end portion non-rotationally connected to a proximal portion of said distractor tip to transmit a rotational force from said handle to said distractor tip, said inner shaft having a proximal connection end portion engaged with said handle and a distal connection end portion selectively and removably connected to said distractor tip; and wherein said distal driving end portion of said outer shaft and said proximal portion of said distractor tip each define driving shoulders positioned in abutment with one another to non-rotationally connect said outer shaft with said distractor tip to transmit said rotational force from said outer shaft to said distractor tip, and wherein said driving shoulders are defined by an axial projection positioned within a drive slot.

10. A spinal disc space distractor, comprising:

a distractor tip; and a shaft assembly extending generally along a longitudinal axis and comprising a handle, an outer tube defining an axial passage and an inner shaft at least partially disposed within said axial passage, said outer tube including a proximal driving end portion non-rotationally connected to said handle and a distal driving end portion non-rotationally connected to a proximal portion of said distractor tip to transmit a rotational force from said handle to said distractor tip, said inner shaft having a proximal connection end portion engaged with said handle and a distal connection end portion selectively and removably connected to said distractor tip; and wherein said proximal connection end portion of said inner shaft is connected to said handle by a connection mechanism, wherein engagement of said connection mechanism with said proximal connection end portion of said inner shaft maintains said distal driving end portion of said outer tube in engagement with said proximal portion of said distractor tip.

11. The distractor of claim 10, wherein said connection mechanism comprise a ball detent connection mechanism comprising at least one ball biased into engagement with said proximal connection end portion of said inner shaft by an outer sleeve positioned over said at least one ball.

12. A spinal disc space distractor, comprising:

a distractor tip; and a shaft assembly extending generally along a longitudinal axis and comprising a handle, an outer tube defining an axial passage and an inner shaft at least partially disposed within said axial passage, said outer tube including a proximal driving end portion non-rotationally connected to said handle and a distal driving end portion non-rotationally connected to a proximal portion of said distractor tip to transmit a rotational force from said handle to said distractor tip, said inner shaft having a proximal connection end portion engaged with said handle and a distal connection end portion selectively and removably connected to said distractor tip; and wherein said outer tube defines a window extending therethrough in a direction transverse to said longitudinal axis and into communication with said axial passage.

13. A spinal disc space distractor, comprising:

a distractor tip; and a shaft assembly extending generally along a longitudinal axis and comprising a handle, an outer tube defining an axial passage and an inner shaft at least partially disposed within said axial passage, said outer tube including a proximal driving end portion non-rotationally connected to said handle and a distal driving end portion non-rotationally connected to a proximal portion of said distractor tip to transmit a rotational force from said handle to said distractor tip, said inner shaft having a proximal connection end portion engaged with said handle and a distal connection end portion selectively and removably connected to said distractor tip; and wherein said outer tube is cylindrical and includes a non-tapering portion adjacent said proximal driving end portion and a tapering portion tapering from a larger diameter adjacent said non-tapering portion to a smaller diameter adjacent said distal driving end portion.

14. The distractor of claim 13, wherein said tapering portion defines a window extending therethrough in a direction transverse to said longitudinal axis and into communication with said axial passage.

* * * * *